(12) United States Patent
Shekalim

(10) Patent No.: US 8,439,879 B2
(45) Date of Patent: May 14, 2013

(54) INFUSION SET OF SELF-OCCLUSION MECHANISM

(75) Inventor: Avraham Shekalim, Nesher (IL)

(73) Assignee: Medx-Set, Haifa (IL)

( * ) Notice: Subject to any disclaimer, the term of this patent is extended or adjusted under 35 U.S.C. 154(b) by 0 days.

(21) Appl. No.: 13/116,033

(22) Filed: May 26, 2011

(65) Prior Publication Data

US 2011/0224601 A1   Sep. 15, 2011

Related U.S. Application Data

(63) Continuation of application No. 12/118,786, filed on May 12, 2008, now Pat. No. 7,951,122.

(60) Provisional application No. 60/917,075, filed on May 10, 2007.

(51) Int. Cl.
     *A61M 5/00*   (2006.01)

(52) U.S. Cl.
     USPC .................................. 604/250; 604/167.02

(58) Field of Classification Search ............ 604/65, 604/174, 250
     See application file for complete search history.

(56) References Cited

U.S. PATENT DOCUMENTS

| | | | |
|---|---|---|---|
| 4,874,377 A * | 10/1989 | Newgard et al. | 604/167.02 |
| 6,126,637 A | 10/2000 | Kriesel et al. | |
| 7,147,615 B2 * | 12/2006 | Wariar et al. | 604/6.16 |
| 2002/0169439 A1 | 11/2002 | Flaherty | |
| 2004/0256004 A1 | 12/2004 | Kessell et al. | |
| 2007/0250007 A1 | 10/2007 | Shekalim | |

* cited by examiner

*Primary Examiner* — Kevin C Sirmons
*Assistant Examiner* — Brandy C Scott
(74) *Attorney, Agent, or Firm* — Mark M. Friedpat

(57) ABSTRACT

A device, system and method for occluding fluid flow through an infusion set detached from a patient's body. The device includes a means for detecting loss of contact to a patient's body and activating an occlusion mechanism accordingly.

11 Claims, 28 Drawing Sheets

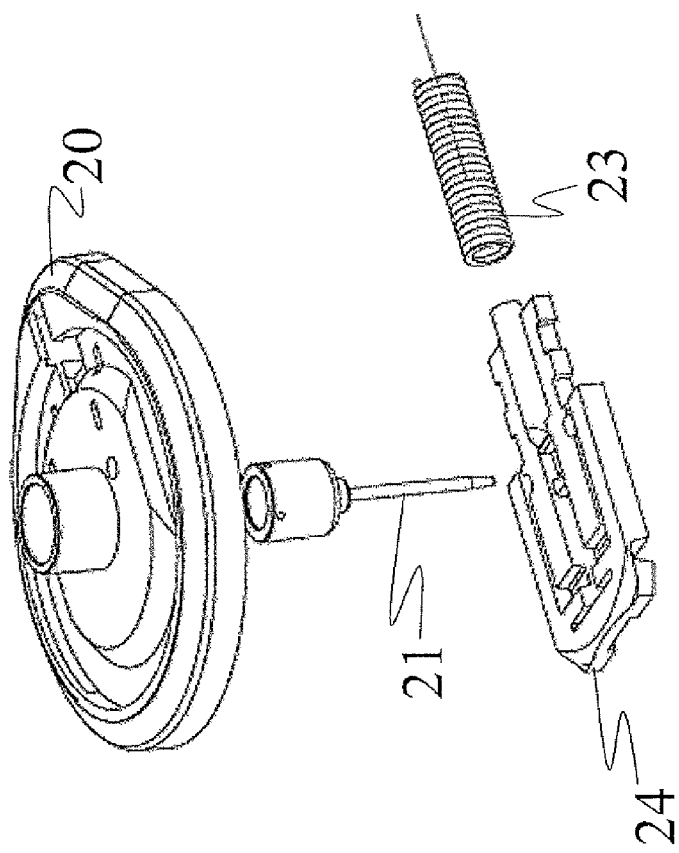
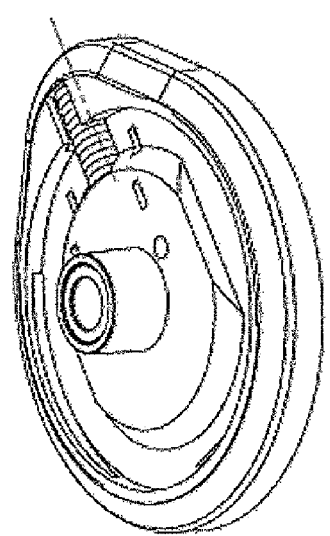
Figure 12

INFUSION SET OF SELF-OCCLUSION MECHANISM

FIELD AND BACKGROUND OF THE INVENTION

The present invention relates to subcutaneous delivery of medication via a drug delivery system and, in particular is concerned with blocking the flow of medication when an infusion set becomes disconnected from the body of the patient. The self-occluding infusion set may be used together with a delivery system sensitive to flow blockage in order to trigger an alarm under circumstances in which the medication would otherwise be delivered outside the patient's body.

It is known that automated drug delivery systems provide a reliable means for administering medication at a prescribed dosage over an extended period. These systems typically include a medication pump connected to an infusion set attachable directly to the patient's body, and a cannula for delivering the medication subcutaneously. Under normal circumstances the medication flows through the system into the patient's body in a controlled and consistent manner. However, such automation alone is not failsafe; fluid flow blockage (occlusion) occasionally occurs, preventing delivery of the medication to the patient. To address such problems, most drug delivery systems include an alarm system designed to alert the user when a blockage occurs so that he may take appropriate measures. Occlusion of the flow path results in a sudden increase in backpressure in the drug outlet flow path, thereby rendering the malfunction relatively easy to detect.

A more problematic situation is caused if the infusion set becomes disconnected from the patient's body. In this case, there is typically no detectable change in operating pressure along the flow path, such that the system may continue to deliver medication outside the body without generating any indication of malfunction. This may leave the patient oblivious to the fact that he is not receiving the required medication, resulting in a potentially life threatening situation even during waking hours and particularly during sleeping hours.

There is therefore a need for an infusion set that facilitates the detection of non-delivery of medication to the patient in situations the infusion set has become disconnected from the body.

SUMMARY OF THE INVENTION

The present invention is a device, a system and a method for occluding fluid flow through an infusion set when the infusion set has become disconnected from a patent's body.

According to the teachings of the present invention there is provided, an infusion set for administering a fluid through the skin, the infusion set comprising: (a) a cannula having a lumen for fluid transfer through the skin; (b) a retention arrangement maintaining an inserted position of said cannula through the skin; and (c) a self-occlusion mechanism associated with said retention arrangement and with said cannula, said self-occlusion mechanism being configured such that, while said retention arrangement maintains an inserted position of said cannula, said self-occlusion mechanism is retained in a first non-occluding state and, if said retention arrangement ceases to maintain the inserted position of said cannula, said self-occlusion mechanism assumes a second state in which said self-occlusion mechanism at least partially occludes fluid flow through said cannula.

According to a further feature of the present invention, an inserter needle initially inserted in the lumen of said cannula such that said inserted needle prevents said self-occlusion mechanism from assuming said second state prior to withdrawal of said inserter needle.

According to a further feature of the present invention the retention arrangement includes an adhesive material applied to the underside of said infusion set.

According to a further feature of the present invention the self-occlusion mechanism includes a biasing element to resiliently bias said mechanism to assume said second state.

According to a further feature of the present invention the biasing element includes a leaf spring.

According to a further feature of the present invention the self occlusion mechanism includes a constriction element to occlude said cannula.

According to a further feature of the present invention the constriction element includes a rotatably mounted cam.

According to a further feature of the present invention the constriction element includes a slideably mounted constriction element.

According to a further feature of the present invention the constriction element is implemented as an integrally biased cannula.

According to a further feature of the present invention the self-occlusion mechanism is configured to fully occlude said cannula.

There is also provided according to the teachings of the present invention a system for detecting disconnection of an infusion set from the skin of a subject, the system comprising: (a) a drug delivery device configured to deliver a controlled flow of a liquid drug, the drug delivery device including an arrangement for detecting occlusion of an outlet flow path; (b) an infusion set connected to said outlet flow path, said infusion set including a cannula for delivering the liquid drug through the skin of the subject; and (c) a self-occlusion mechanism associated with said infusion set, said self-occlusion mechanism being configured such that, when said cannula is removed from the skin of the subject, the self-occlusion mechanism at least partially occludes fluid flow through said infusion set.

There is also provided according to the teachings of the present invention a method for facilitating detection of malfunction during delivery of a drug via an infusion set through the skin of a patient, the method comprising the steps of: (a) providing a flow-path from a drug delivery device via an infusion set through the skin of the patient;

(b) providing a flow-path from a drug delivery device via an infusion set through the skin of the patient; (c) responsive to at least partial failure of said retention arrangement to retain the part of the infusion set secured against with the skin, generating at least partial occlusion of the flow path.

BRIEF DESCRIPTION OF THE DRAWINGS

The invention is herein described, by way of example only, with reference to the accompanying drawings, wherein:

FIG. 12 is an exploded view of a third slideable-block variant form of a constriction-based embodiment of a self-occluding infusion set.

DESCRIPTION OF THE PREFERRED EMBODIMENTS

Figure 1:
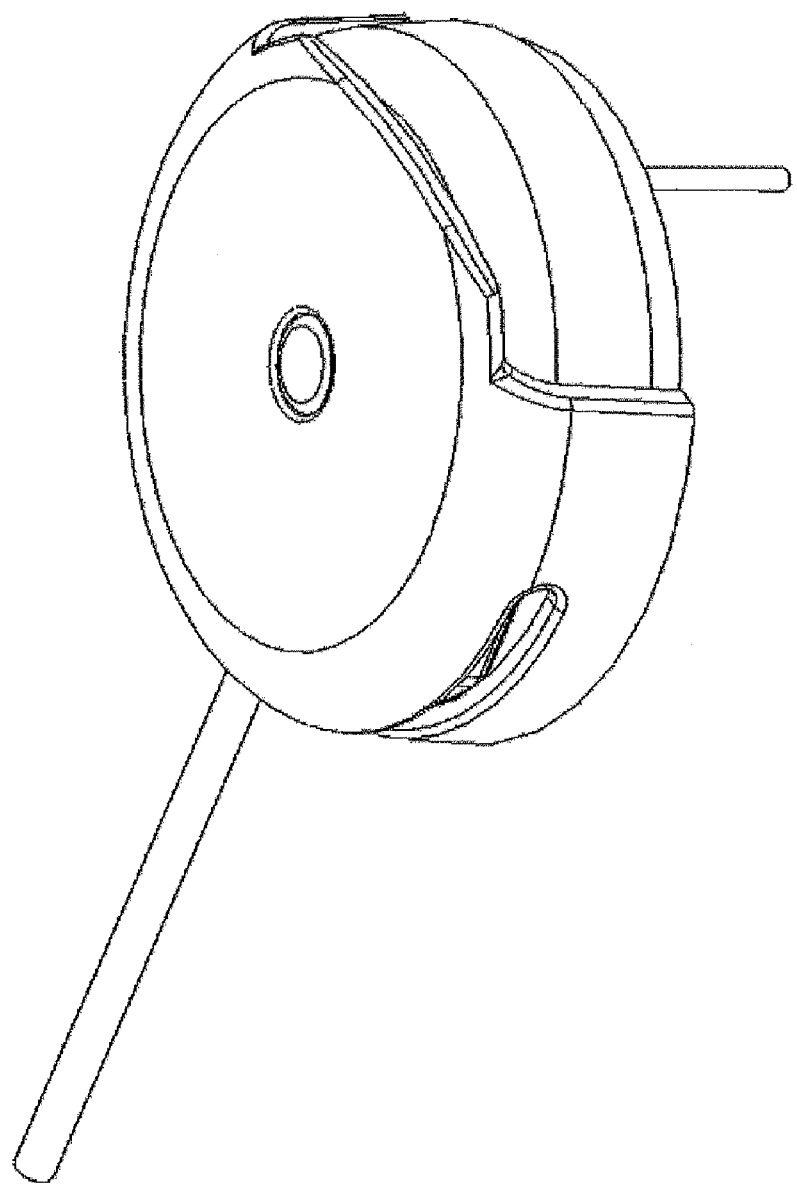
FIG. 1 is an isometric view of a cam variant of a constriction-based embodiment of an infusion set.

The present invention is a mechanism, system, and corresponding method for a drug delivery system for automatically occluding fluid flow through an infusion set when the cannula becomes disengaged from a patient.

The principles and operation of the various implementations according to the present invention may be better understood with reference to the drawings and the accompanying description. The mechanism of the present invention will be illustrated herein with reference to a number of non-limiting examples. Three general embodiments, based on the manner of occlusion, will be described in reference to the figures as follows:

A first implementation constricts a flow passageway, i.e., deforms a wall of the passageway by application of external forces sufficient to substantially occlude flow, as will be described with reference to FIGS. 1-7.

A second implementation introduces an obstruction so as to substantially block a flow passageway, as will be described with reference to FIGS. 8-25.

A third implementation kinks or otherwise deforms the shape of a flow passageway, which may be the projecting portion of the cannula, as will be described in reference to FIGS. 26-27.

Although the invention will be described with reference to particular occlusion mechanisms falling within one of the above groups, it should be noted that the invention is not limited to these implementations, and may be implemented using any mechanism effective to selectively occlude some part of the drug delivery flow path, as will be clear from the following description.

Before addressing the details of the exemplary embodiments, it should be appreciated that, as mentioned above, all of the various embodiments share a common operational principle, corresponding to a device, system and method of the present invention. Specifically, as noted above, it is common for drug delivery systems to include an arrangement for detecting blockage of the flow path and generating an alarm to the user, whereas inadvertent disconnection of the infusion set from the body is more difficult to reliably detect. To address this problem, the present invention provides an infusion set modified by a self-occlusion mechanism configured to block flow through the infusion set in the event that the infusion set becomes disconnected from the body. This converts the hard-to-detect condition of disconnection into the easier-to-connect condition of occlusion, thereby facilitating detection of the malfunction and timely warning to the user.

Although the invention is described herein in preferred implementations in which the flow through the infusion system is typically completely occluded, it should be noted that implementations causing partial occlusion are also within the scope of the invention. Incomplete occlusion sufficient to cause increased back-pressure in the drug delivery flow path is also detected by many drug delivery systems as an error condition requiring intervention, and may therefore be used in the context of the present invention.

It should be noted that the terms "disconnected" or "detached" refer to a loss of contact between the infusion set and the body sufficient to impact the position of the cannula. Therefore, for the purposes of this definition there is no distinction made between a situation in which the infusion set together with the cannula loose complete contact with the body and a situation in which the infusion set looses contact while the cannula remains inserted because the cannula will inevitably be withdrawn from patient's body almost immediately after the infusion looses contact. Furthermore, a condition in which the infusion set remains partially in contact with the body but no longer provides reliable positioning of the cannula is also referred to as "disconnected" or "detached".

Furthermore, regarding terms of usage, the term "self-occluding" refers to any functionality provided by any combination of elements included within or externally associated with the infusion set eliminating the need for manual intervention for occluding fluid-flow through the infusion set.

In certain cases, an electrically or otherwise remotely operable flow occluding device may be actuated in response to sensing of disconnection of the infusion set from the body.

Following is a general description of the structure common to all of the embodiments presented here within.

The self-occluding infusion set is a device for administering a fluid through the skin; including a cannula having a lumen for fluid transfer through the skin, a retention arrangement providing the infusion set attachment to the body so as to maintain an inserted position of the cannula through the skin; and a self-occlusion mechanism associated with the retention arrangement and with the cannula so that the self-occlusion mechanism is configured such that, while the retention arrangement provides attachment of the infusion set to the body, the self-occlusion mechanism is retained in a first non-occluding state and, if the retention arrangement ceases to provide attachment to the body, the self-occlusion mechanism assumes a second state in which the self-occlusion mechanism occludes fluid flow through the cannula. The current invention occludes flow through the cannula by occluding the fluid flow passageway at any point along the flow passageway as will be evident in the following implementations.

Turning now to FIGS. 1-4, a first cam form of a constriction-based implementation of the present invention includes a cannula 3, a constriction cam 4 for occluding fluid flow through the cannula 3, a cam lever 5 for detecting proximity to the patient's body, a cam lever recess 6, and a leaf-spring 7 for biasing the cam lever 5. The constriction cam 4 is rotatably mounted on the underside of the unit so that it has the angular freedom of motion enabling it to rotate in a first direction to the point in which the cam 4 constricts the cannula 3 and to rotate in the opposite direction thereby moving the cam 4 away from the cannula 3.

Figure 2:
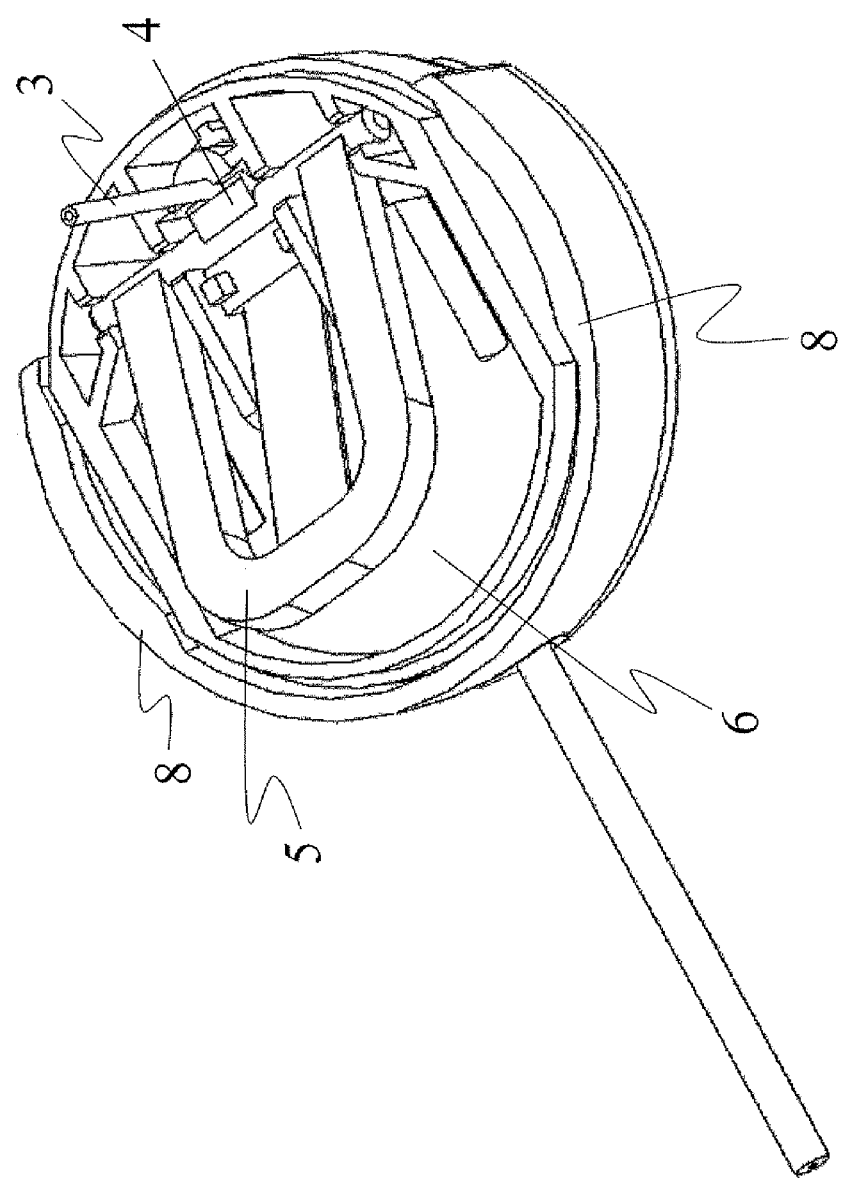
FIG. 2 is an isometric view of the underside of the cam variant of a constriction-based embodiment of an infusion set.
Figure 3:
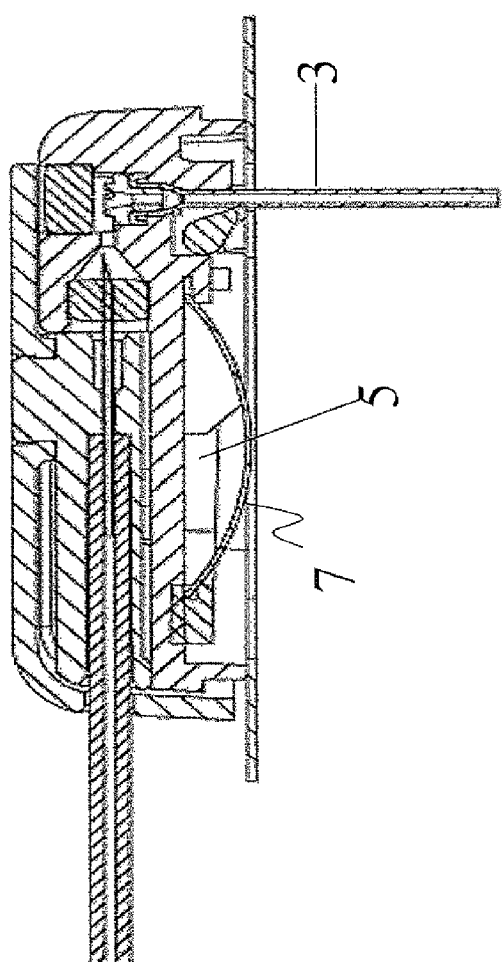
FIG. 3 is sectional view of the can variant of the constriction-based embodiment.
Figure 4A:
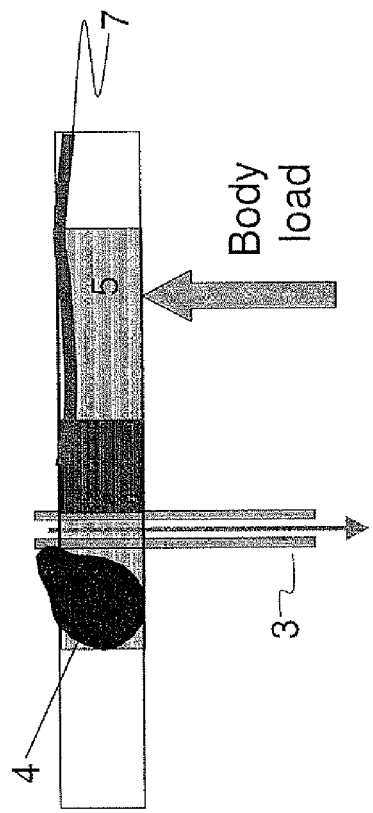
FIGS. 4A and 4B are schematic drawings of the cam variant of the constriction-based embodiment depicting a leaf-spring configuration in its loaded and unloaded states respectively.
Figure 4B:
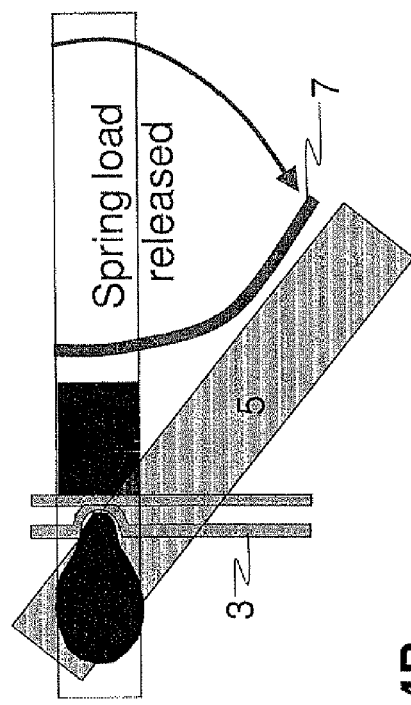

The cam lever 5 is connected on the constriction cam 4 so that the lever's substantially vertical motion in reference to the horizontal plane defined by the underside of the unit translates into angular motion of the constriction can 4. The cam lever 5 is disposed on the constriction can 4 so that when the lever 5 is seated in the cam lever recess 6 the constriction cam 5 is disposed away from the cannula 3 and when the cam lever 5 is situated outside of the recess 6, the constriction can is disposed to occlude the cannula 3. A leaf spring 7 biases the cam lever 5 so that the default position of the cam lever 5 is outside of the lever recess 6. An adhesive material is applied to the bottom surface 8 of the infusion unit to retain the infusion unit on the patient's body. The constriction cam 4 is configurable to constrict the cannula 3 by rotating in a clockwise direction as shown if FIGS. 4A and 4B or in a counter clockwise direction as shown in FIGS. 2 and 3. The amount of torque needed to sufficiently constrict the cannula is a function of the ease of wall deformation of the cannula 3.

Turning now to the operation of the device, in the default configuration the cam lever 5 protrudes from the lever recess 6 and the constriction cam 4 is disposed in its occluding position. Upon attachment the unit the patient's body pushes the cam lever 5 into the cam lever recess 6 and correspondingly rotates the constriction cam 4 away from the cannula 3 enabling the uninhibited flow of medication. The cannula 3 is inserted into the patient's body with an insertion needle as most clearly shown seen in FIG. 6 designation 11. When the unit detaches from the patient's body the constriction lever 5 is free to rotate into its biased position thereby rotating the constriction cam 5 to the point at which it applies sufficient force to constrict the cannula 3. The resulting pressure increase then trips the system's traditional pressure responsive alarm.

Figure 5:
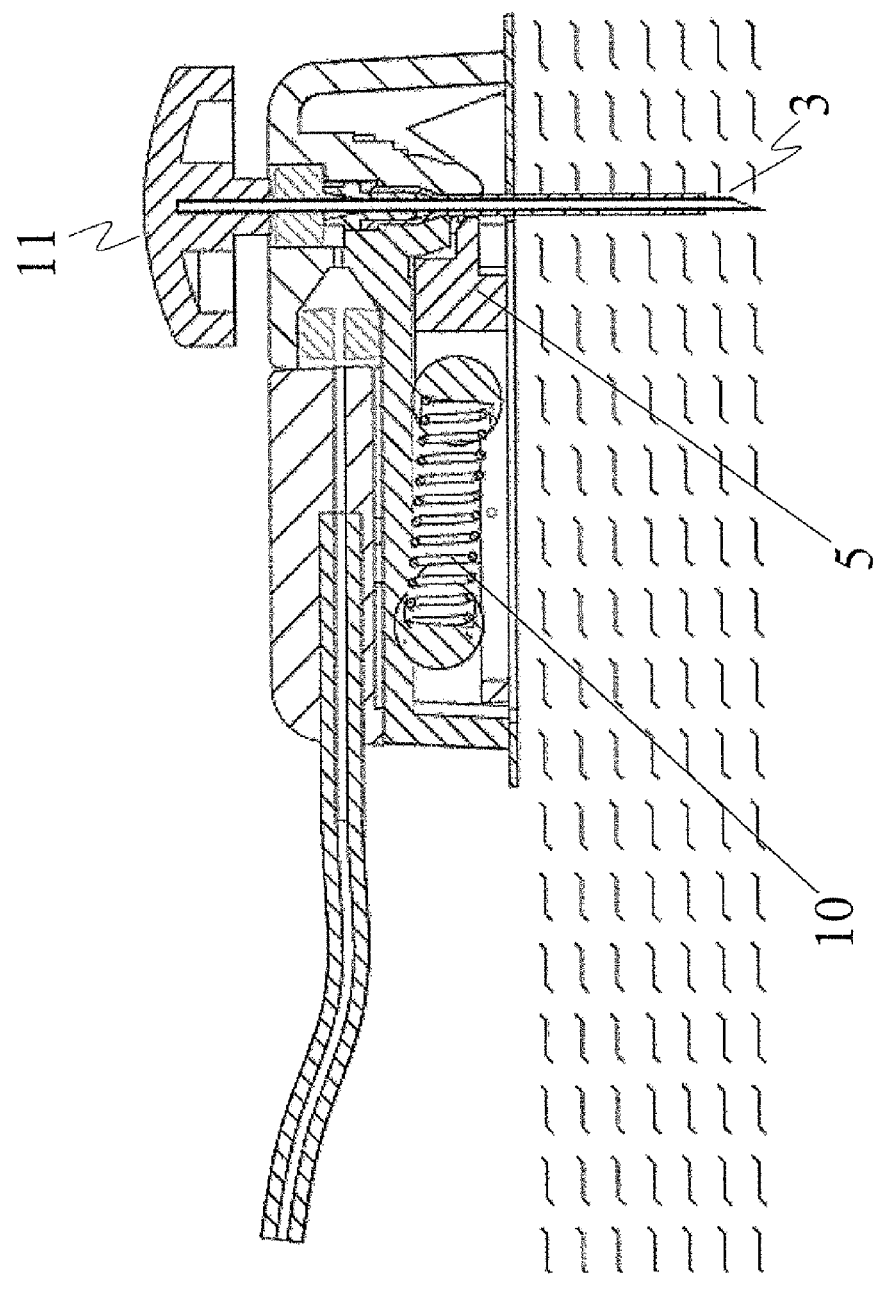
FIGS. 5 through 7 are sectional views of a variant form of the constriction-cam embodiment in its insertion state, non-occluded operative state and detached occluded state, respectively.
Figure 6:
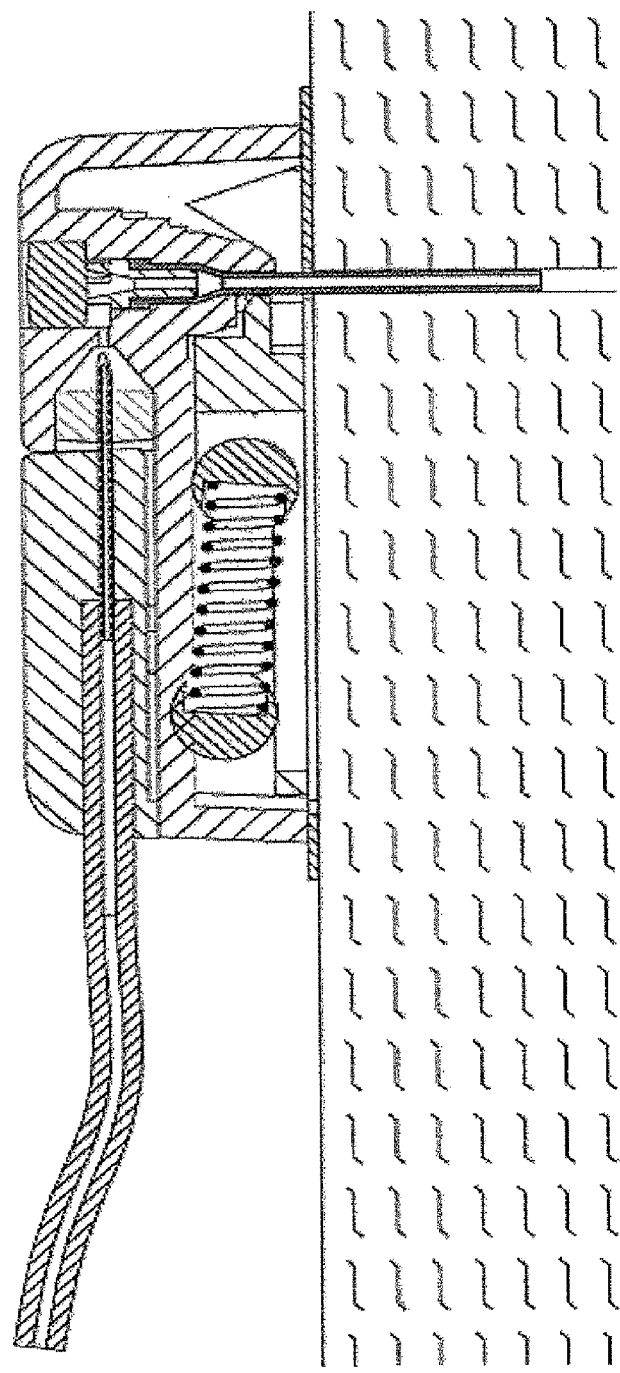
Figure 7:
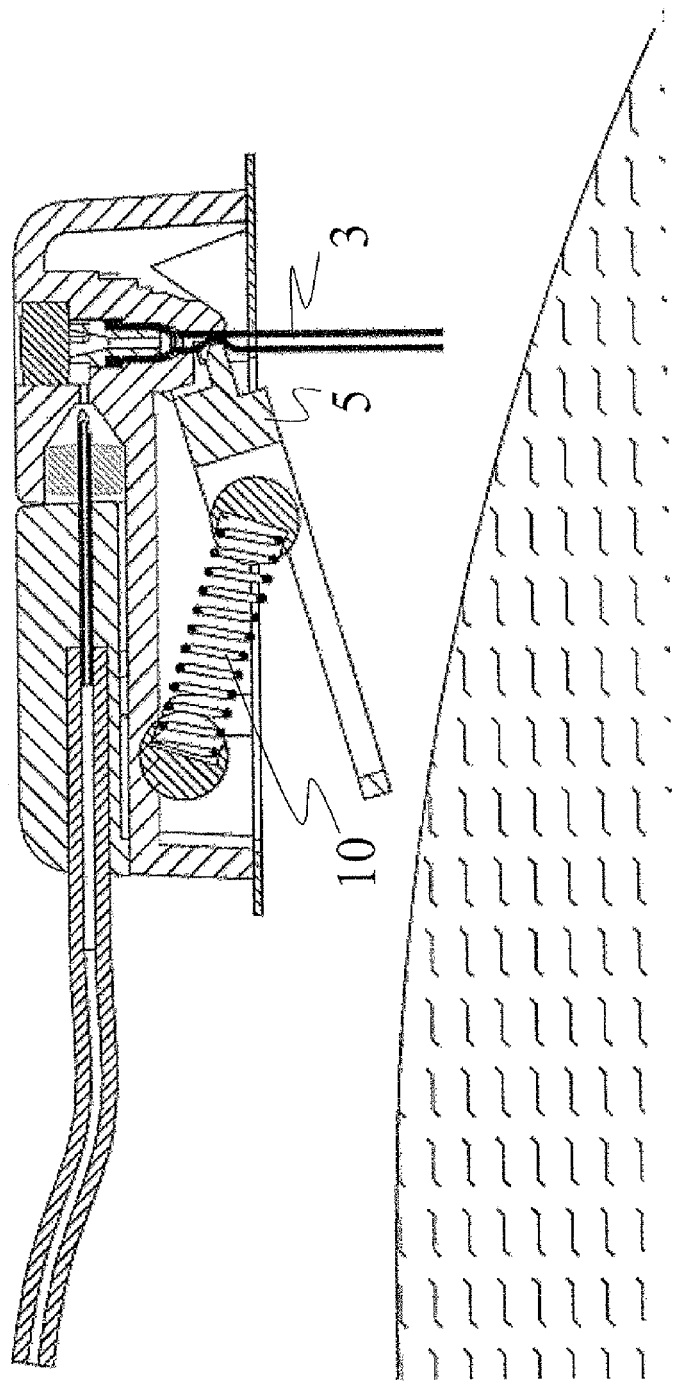

FIGS. 5-7 depict a second cam variant form of the constriction-based embodiment including a pivotally mounted constriction lever 5 for occluding the cannula 3, a compression spring 10 for biasing the constriction lever 5 into a default occluding position.

The compression spring 10 is disposed at a near horizontal angle relative to the horizontal plane defined by the base of the unit thereby variably biasing the constriction element 5 so that it applies a minimum force to the patient's body while attached and applies an increasing force to the cannula 3 is it rotates so that the maximum constricting force is applied to the cannula 3 when the constriction lever has achieved the maximum degree of rotation. This functionality is a result of an increasing horizontal component of the force applied by the spring 10 to the constriction element 5 as the angle between the constriction element 5 and the spring 10 increases. This feature ensures that the constriction element 5 does not push the infusion set off the body while still developing sufficient torque to constrict the cannula 3. It should be noted that the variable bias feature is preferably incorporated in all the embodiments employing a bias element to detect loss of contact with the patient's body.

Figure 8:
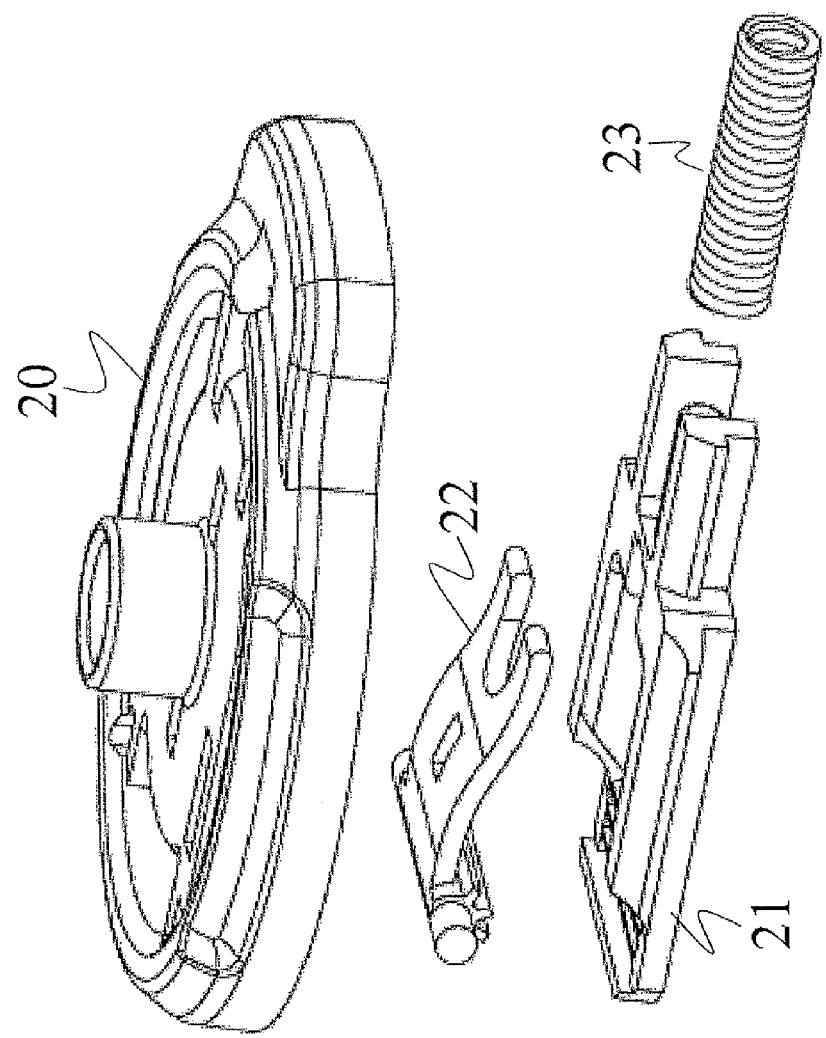
FIG. 8 is an exploded isometric view of a slideable-block variant of the constriction-based embodiment of a self-occluding infusion set.
Figure 9:
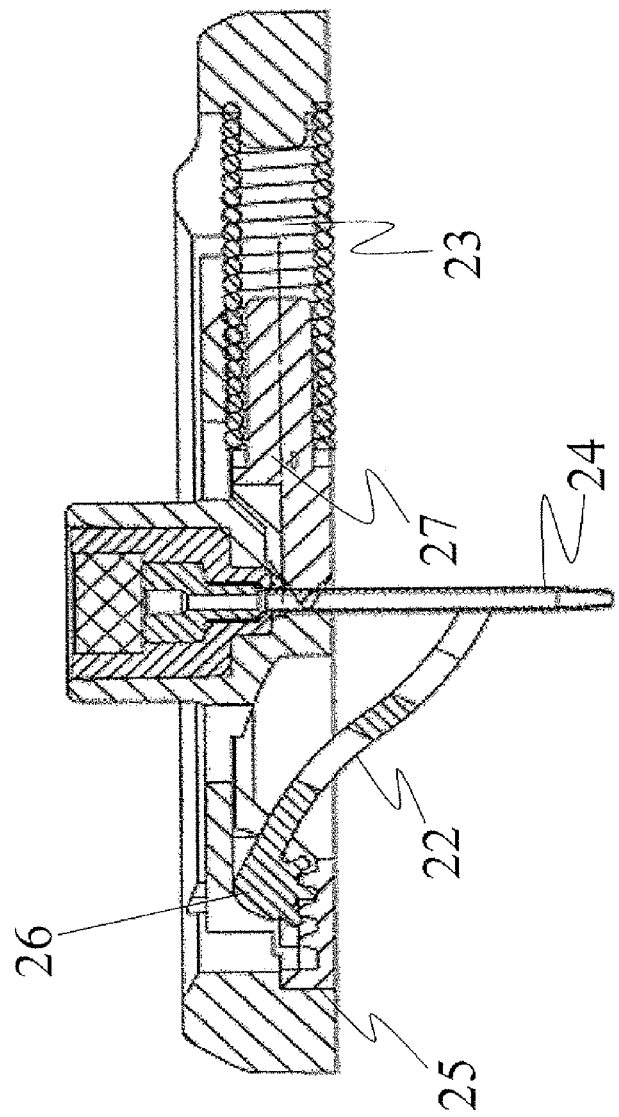
FIGS. 9 and 10 are sectional views of the infusion set of FIG. 8 assembled, shown in its occluded and non-occluded states, respectively.
Figure 10:
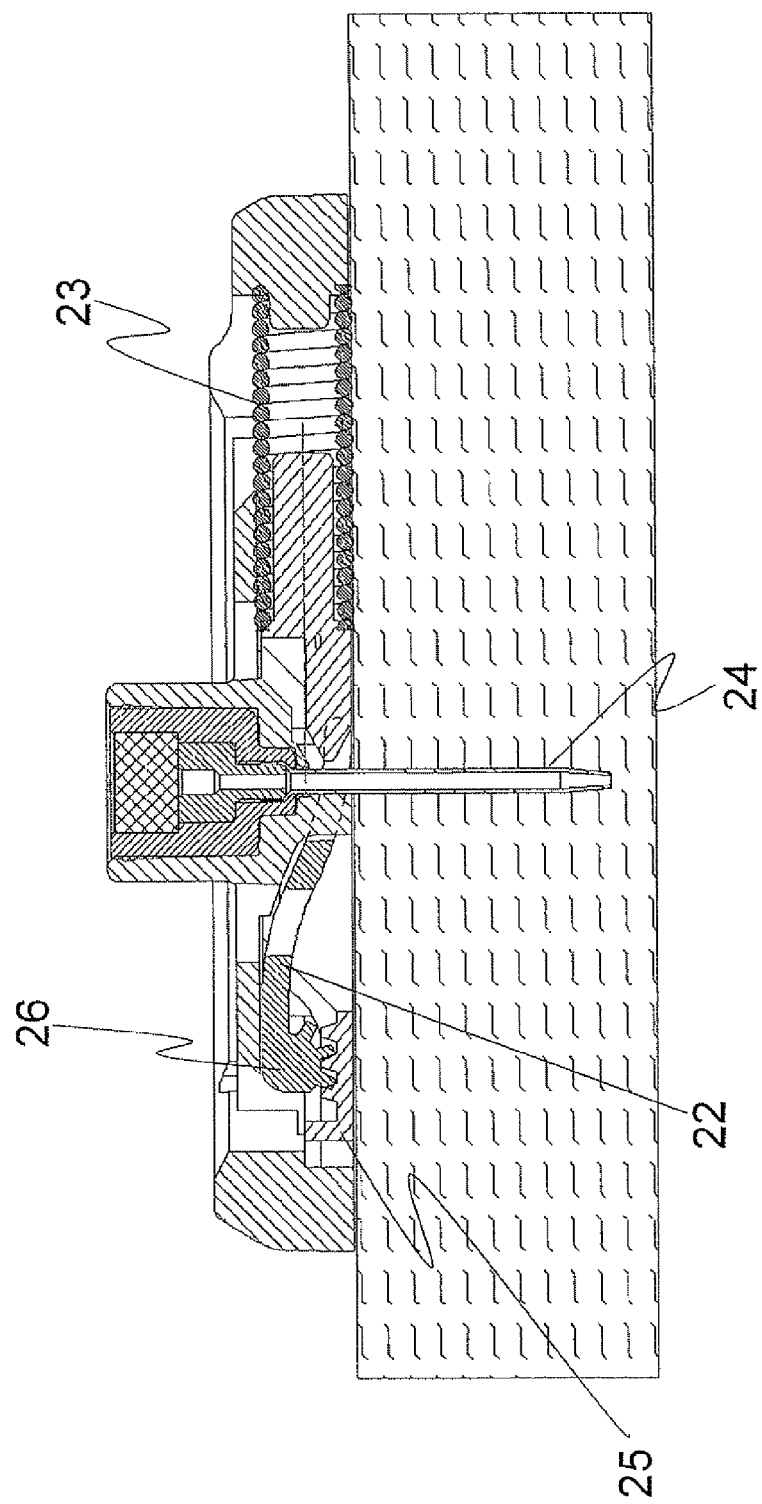

FIGS. 8-10 illustrate a slideable-block form of a constriction-based embodiment include an infusion set housing 20, a slideable-block structure 21, a cannula 24, a lever 22 for detecting proximity to the patient's body, a geared axle 26 connected to lever 22 for translating substantially vertical motion of the lever 22 into lateral motion of the slideable-block structure 21, and a compression spring 23 for resiliently biasing the slideable block structure 23 into a default occluding position. The slideable block structure 23 includes a toothed interface 25 for the intermeshing of a geared axle 26, a spring guide 27, a lip structure 28 for communicating with a corresponding lip structure along the inner wall of the unit housing 20. The slideable block structure 21 is disposed in the infusion set housing 20 so as to slide horizontally along the length of the unit. The horizontal mobility is provided by the block structure lip 28 communicating with the corresponding unit housing lip (not shown). The compression spring 23, disposed in the block structure 27, resiliently biases the block structure 21 into a default occluding position. The geared axle 26 with the attached lever 22 is seated in the block-structure toothed interface 25 so as to translate substantially vertical motion of the attached lever 22 into lateral motion of the block structure 21 and vice versa. The lever 22 is disposed so that while the block structure 21 is in its default occluding position the lever 22 correspondingly protrudes from the underside of the unit and as the lever 22 rotates into the underside of the unit the block structure 21 moves laterally away from the cannula 24 enabling the free flow of liquids. It should be noted that all of the slideable-block embodiments slide along a corresponding lip appropriately disposed along the inner wall of the unit housing.

As mentioned above the operation of the device is analogous in each of the embodiments and their variants.

Figure 11:
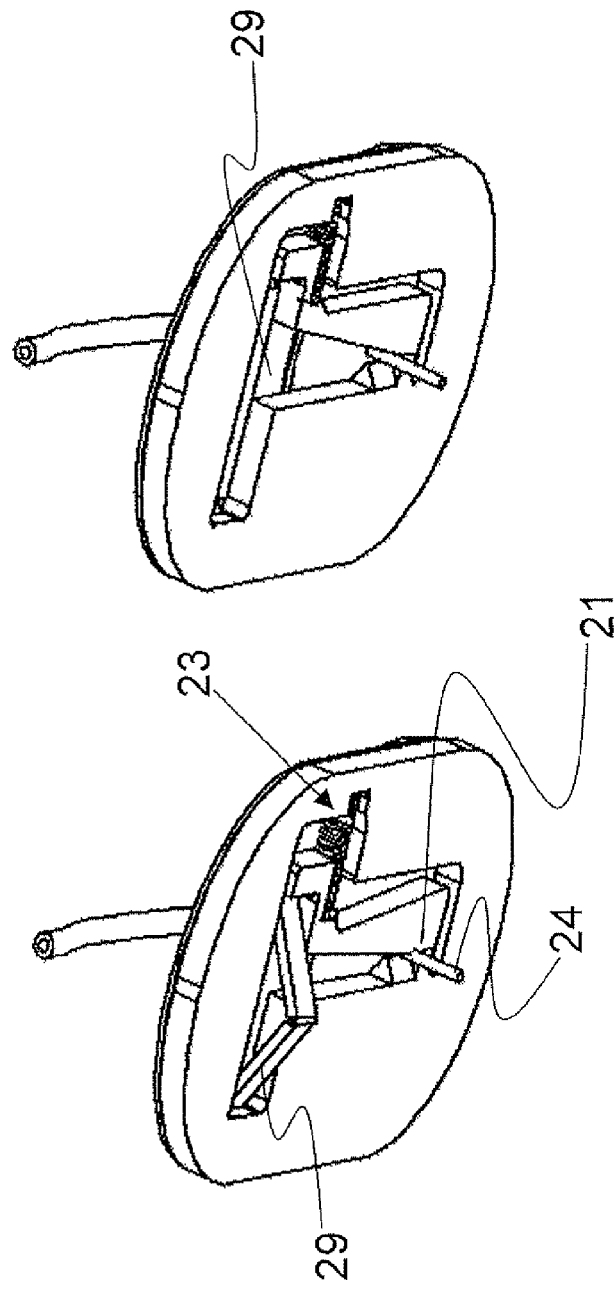
FIGS. 11A and 11B depict the underside of a second slideable-block variant form of the constriction-based embodiment in its occluded and non-occluded states.

FIG. 11 illustrates a second slideable-block variant form of a constriction-based embodiment including a cannula 24, a foldable element for translating proximity to the patient's body to proximity of the slideable block-structure 21 to the cannula, a slideable block structure 21 and a compression spring 23 for biasing the slideable block-structure 21 into a default occluding position. The foldable element 29 includes two sequentially and pivotally connected segments configured to assume either a partially folded or a fully extended configuration. The foldable element 29 is operative to assume a partially folded, protruding configuration when the slideable block structure is in its default occluding position and to assume a fully extended, non-protruding configuration when the slideable block structure 21 has assumed a non-occluding position.

Figure 13B:
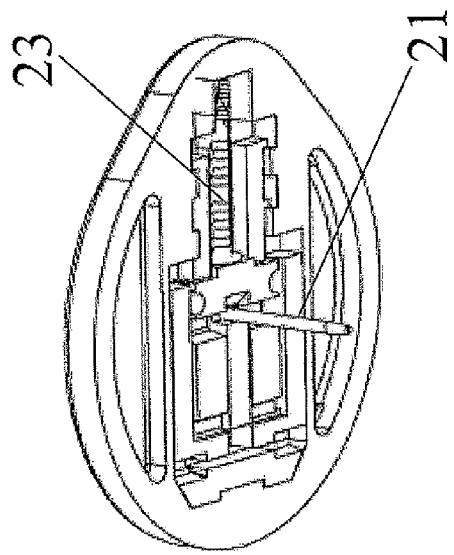
FIGS. 13A and 13B are underside views of the infusion set of FIG. 12 assembled, shown in its occluded and non-occluded states, respectively.
Figure 13A:
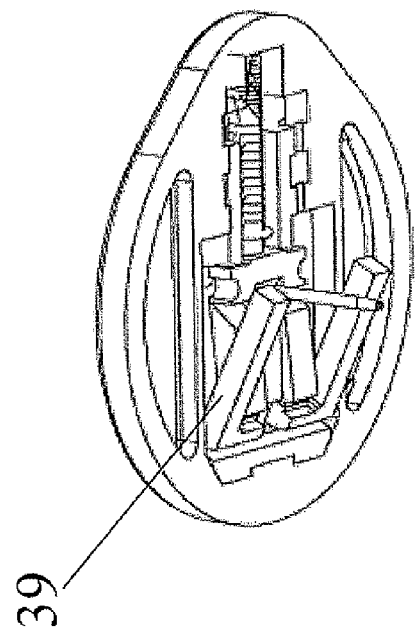
Figures 14A, 14B:
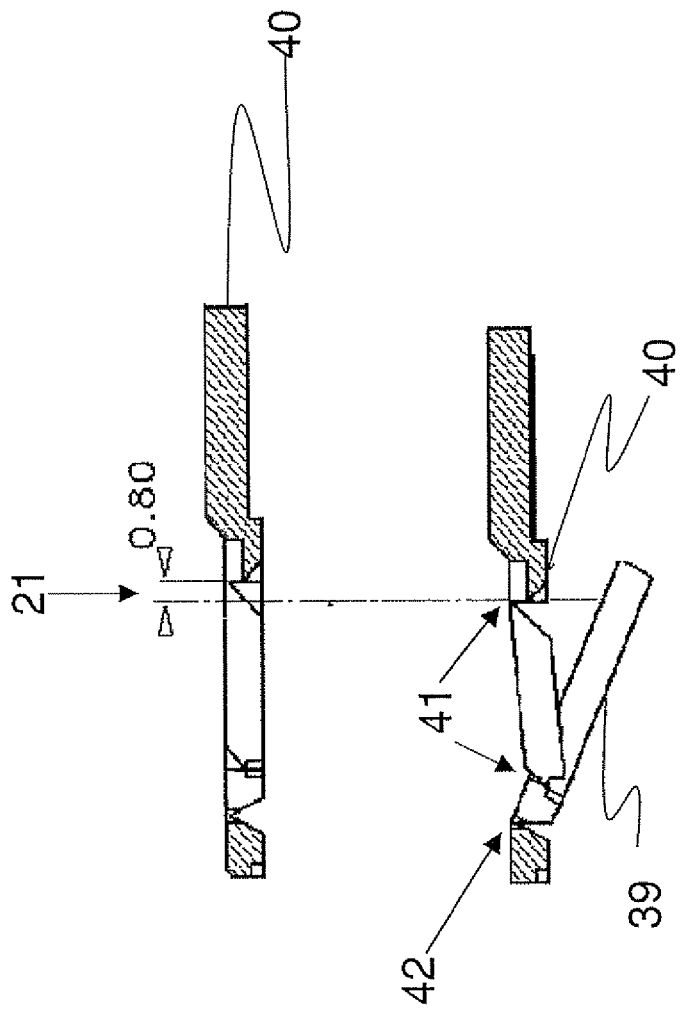
FIGS. 14A and 14B are views of a third slideable-block variant form of a constriction-based embodiment of a self-occluding infusion set showing an integral hinge arrangement in its occluded and non-occluded states, respectively.

FIGS. 12-14 illustrate a third slideable-block variant form of a constriction-based embodiment employing a three-segment structure integrally connected so as to form an effective hinge at each junction. This variant form includes a slideable constriction element 40 for constricting the cannula 24, position transformation members 41 and 39 for transforming a position of a proximity to the patient's body into a corresponding position of the sliding constriction element 40, a compression spring 23 for biasing the constriction element 40 into a default occluding position. Prior to attachment to the patient's body, the compression spring 23 biases the constriction element 40 to slide along a track disposed along the inner wall of the unit housing 20 so as to occlude the cannula 21 and furthermore to cause element 41 to pivot at integral joint 42 so as to be disposed at an angle causing proximity element 39 to pivot at integral joint 43 away from the underside of the unit. This is the default occluding position the unit assumes when unattached to the patient's body. Upon attachment to the patient's body the elements pivot in opposite directions thereby sliding the constriction element 40 into its non-occluding position allowing the uninhibited flow of liquids through the infusion set.

Figure 15:
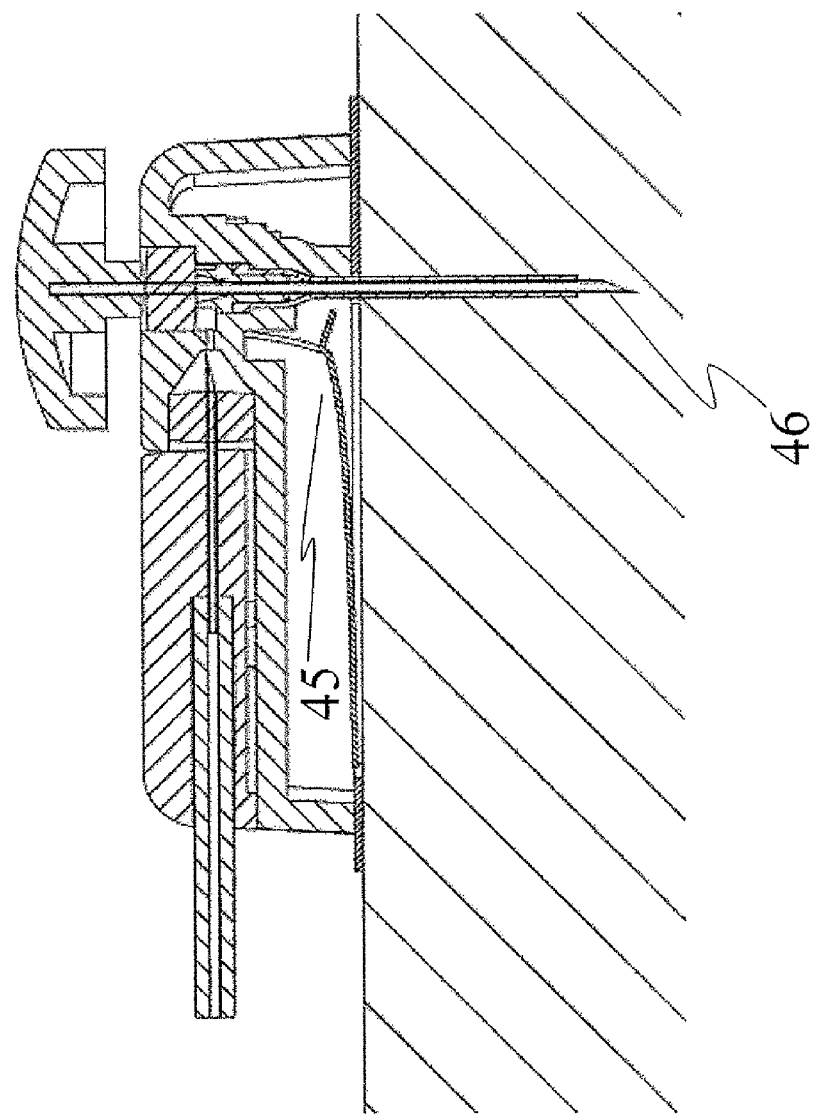
FIGS. 15 through 17 are sectional views of a spring variant form of the constriction-based self-occluding infusion set shown in its insertion state, its non-occluded operating state and its detached occluded state, respectively.
Figure 16:
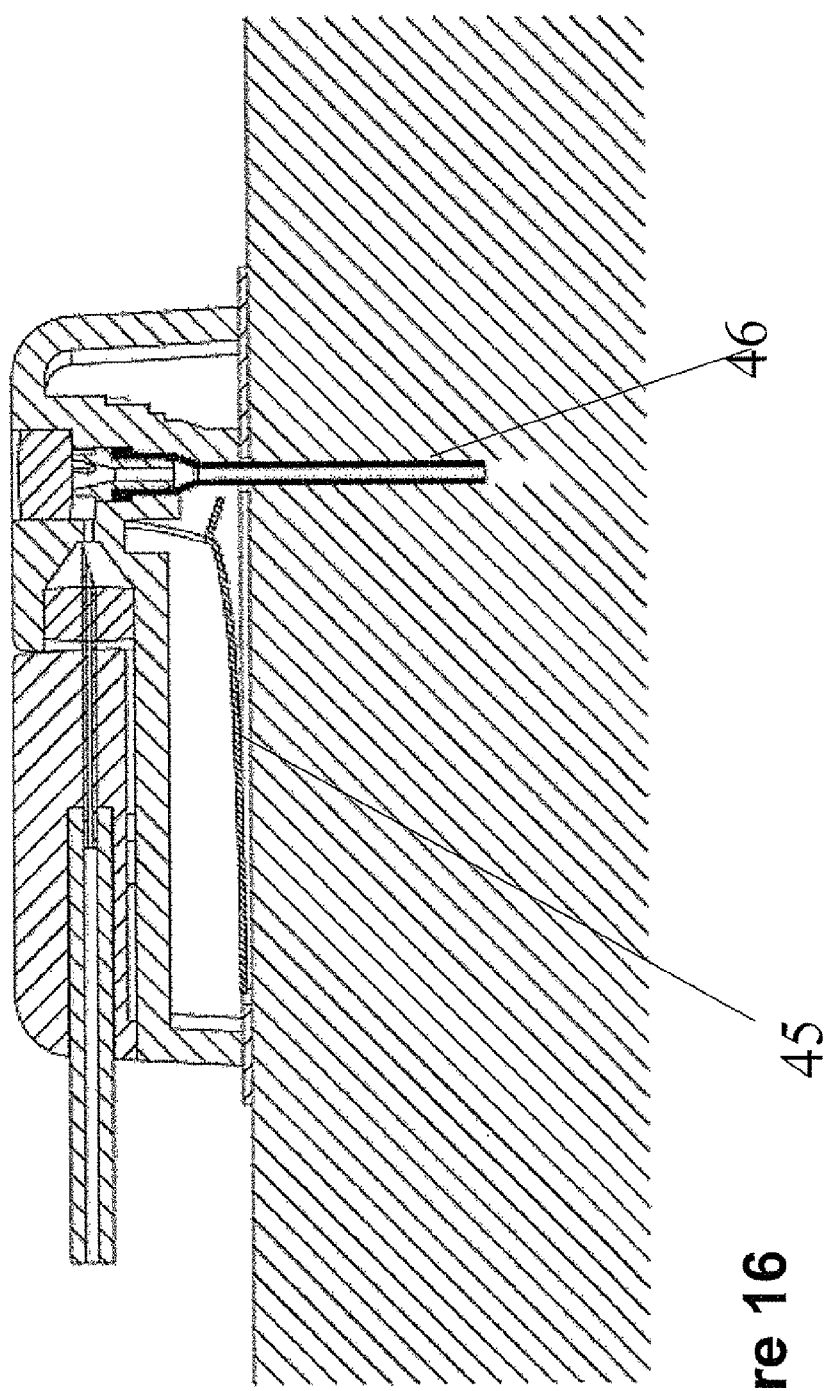
Figure 17:
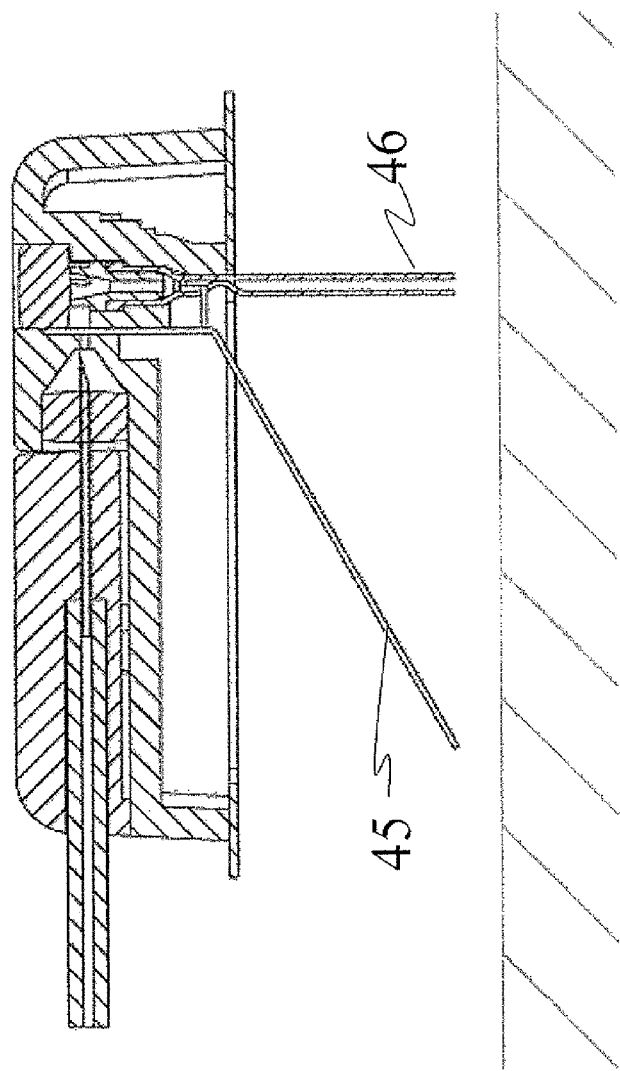
Figure 18:
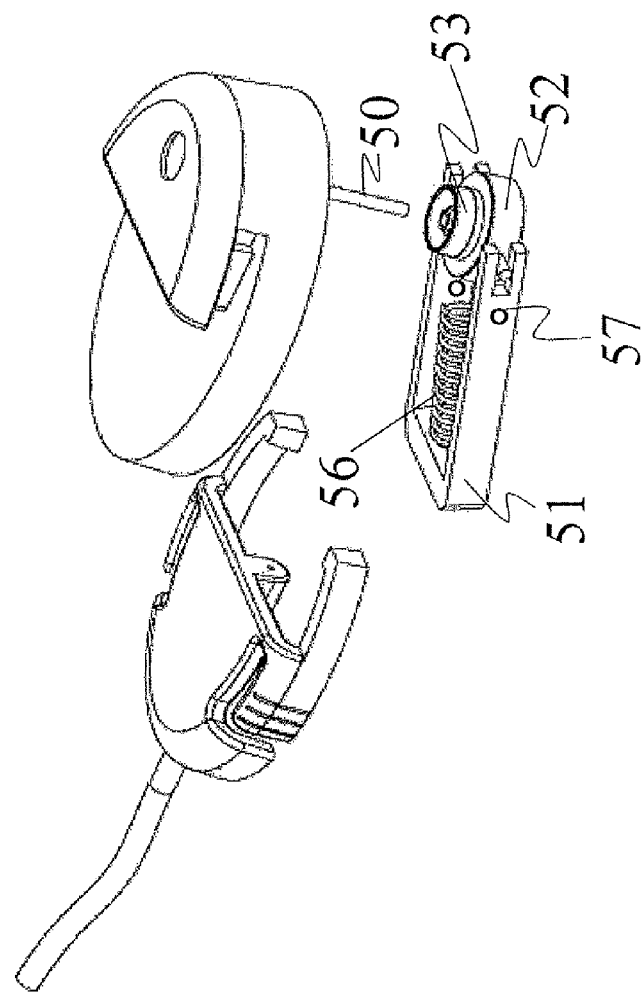
FIG. 18 is an exploded isometric view of a first form of a blockage-based embodiment of the self-occluding infusion set.
Figure 19:
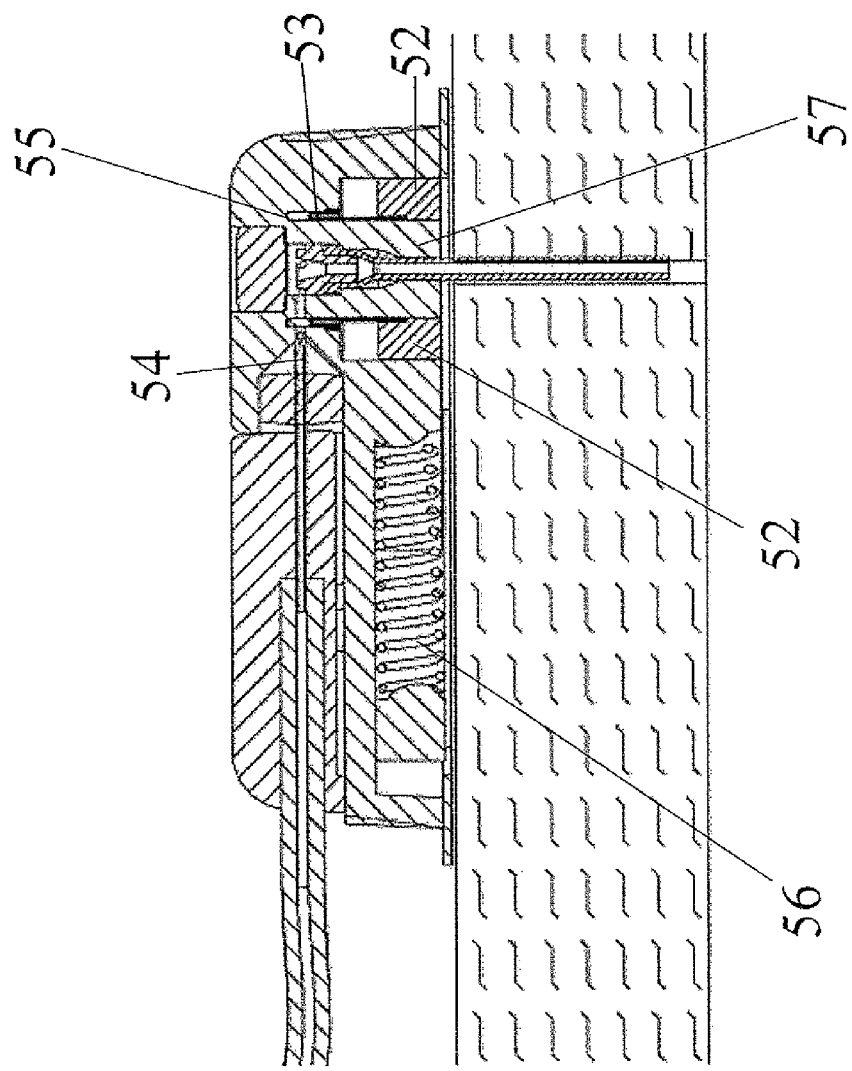
FIG. 19 is a sectional view of the infusion set of FIG. 18 assembled, in its operative, un-occluded state.
Figure 20:
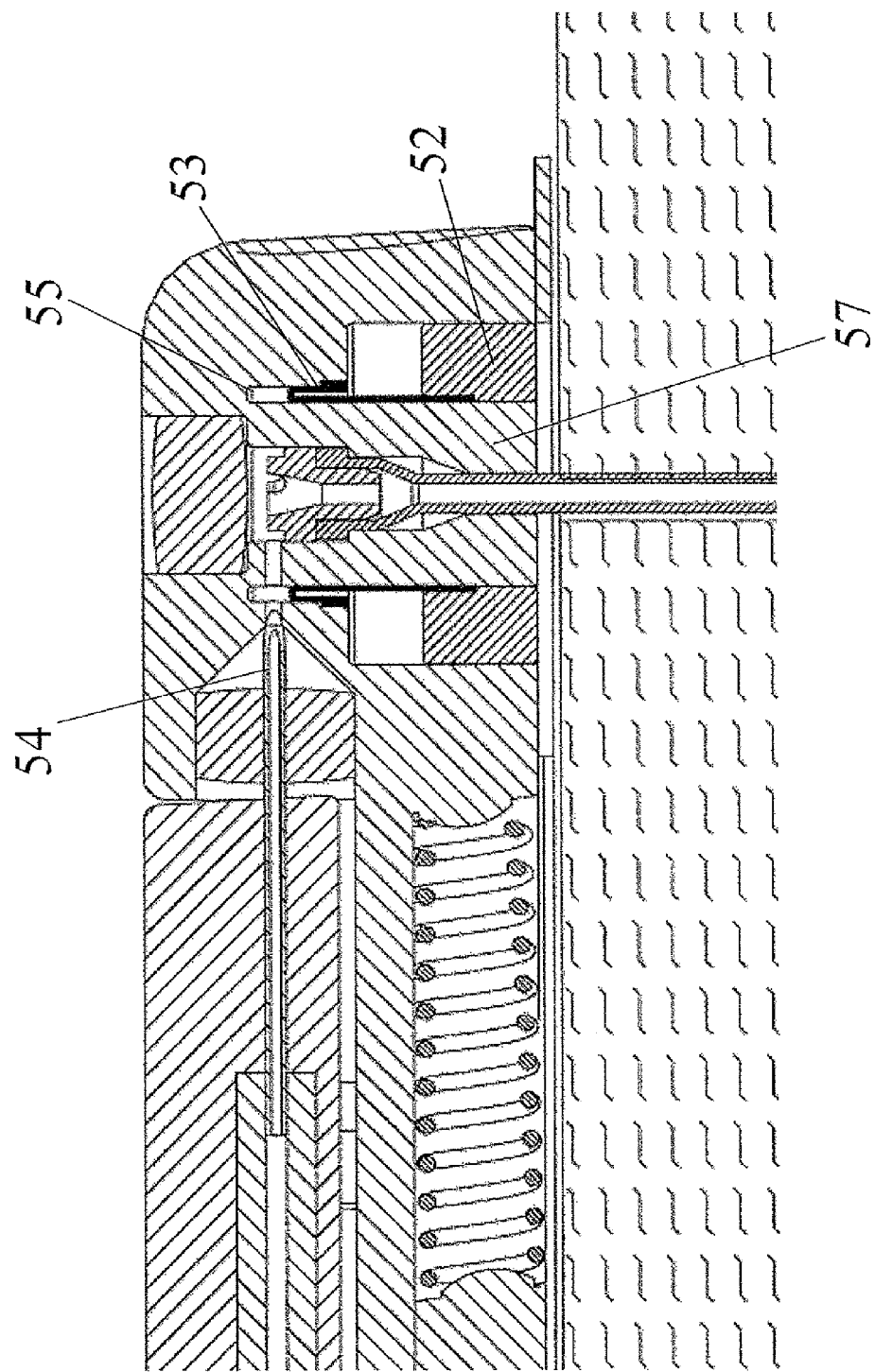
FIG. 20 is a close-up sectional view of the infusion set of FIG. 19.
Figure 21:
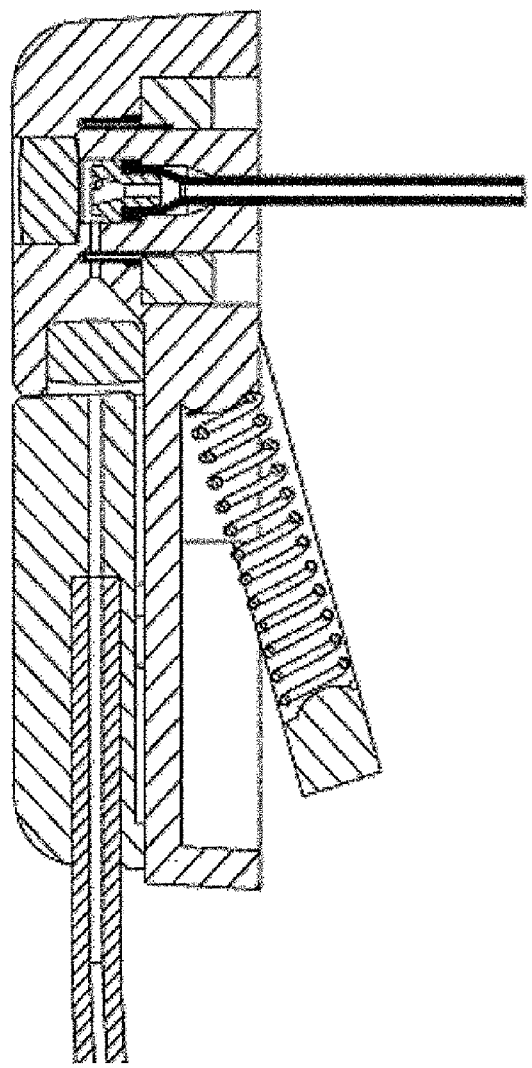
FIG. 21 is a sectional view of the infusion set of FIG. 18 in its assembled, in its operative, un-occluded state.
Figure 22:
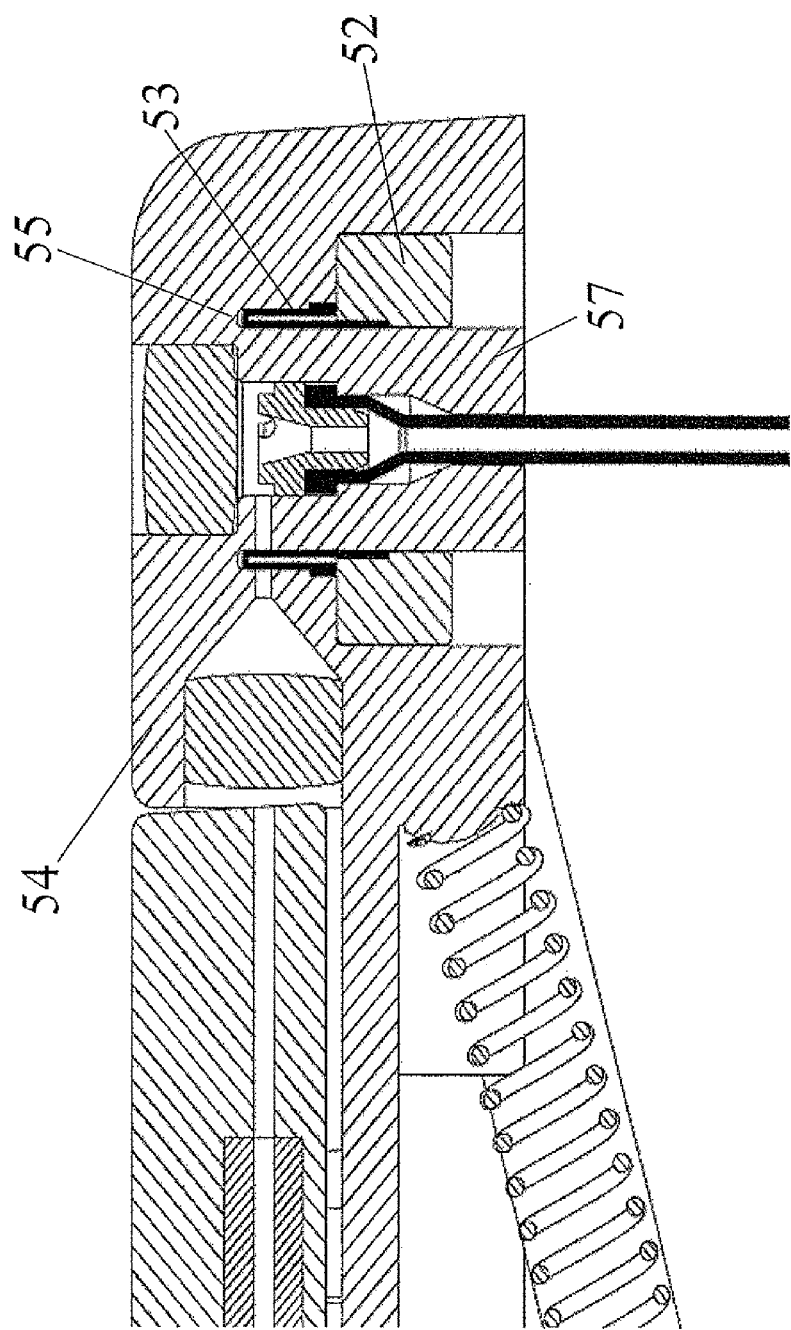
FIG. 22 is a close-up sectional view of the infusion set of FIG. 21.

FIGS. 15-17 illustrate a spring variant form of a constriction-based embodiment employing a leaf spring 45 as the occluding element. The leaf spring is configured so that when the infusion set in unattached to the patient's body the leaf spring is resilient biased to press against the cannula 46 thereby occluding it and when the infusion set is attached to the patient's body, the body pushes leaf spring away from the cannula thereby allowing the uninhibited flow of liquids FIGS. 18-22 illustrate a first form of blockage-based embodiment employing a sleeve diaphragm to block fluid flow through the infusion set. This embodiment includes a cannula 50, a constriction lever 51, a compression spring 56, a flow capillary 54, a sleeve shaped diaphragm 53, a block structure 57 for anchoring the lower edge of the diaphragm 53, a vertically displaceable collar 52 for adjusting the height of the diaphragm 53 and a diaphragm groove 55, The sleeve is disposed vertically around the block structure 57. The lower edge encircling the block structure 57 is fastened to the block structure 57 and the upper edge is folded over so that it extends downward along the outer surface of the inner fold and fastened to the displaceable collar 52. Such a configuration provides a height adjustable diaphragm 53 being heightened or being lowered as the displaceable collar 52 advances upwards or downwards. A circular groove 55 is formed in the infusion set above the line of motion of the diaphragm. The diaphragm fold meshes with this groove when the diaphragm is disposed in its uppermost position.

A capillary bore through the body of the infusion set serves as a fluid passageway 54. The bore is disposed to intersect the diaphragm groove 55 so that the upper surface of the diaphragm fold serves as the bottom portion of the passageway wall while the diaphragm is disposed in its lowest position. When the diaphragm is disposed in its uppermost position the diaphragm meshes with diaphragm groove 55 thereby blocking the passage of liquids. The displaceable collar 52 is pivotally connected to the resiliently biased lever 51 so as to upwardly displace the collar 52 upon detachment of the infusion set from the patient's body thereby occluding the flow passageway 54.

Figure 23:
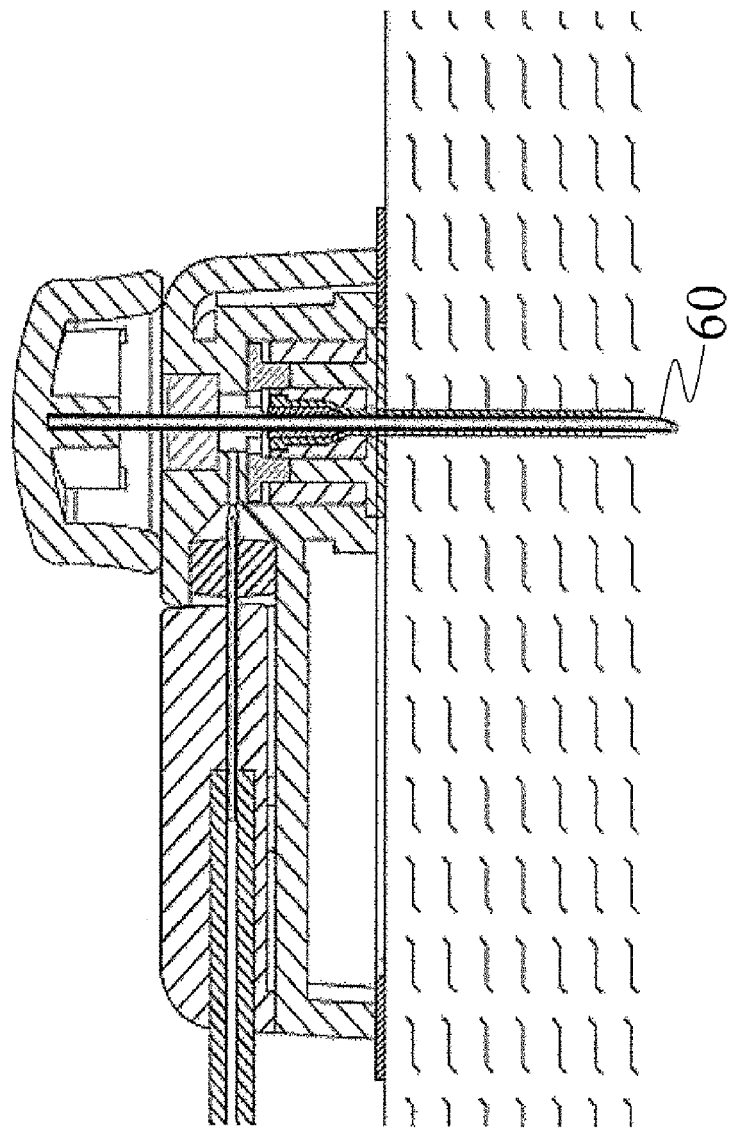
FIGS. 23-25 are sectional views of a second variant form of a blockage-based embodiment of an infusion set in its insertion state, operative non-occluded state, and occluded state, respectively.
Figure 24:
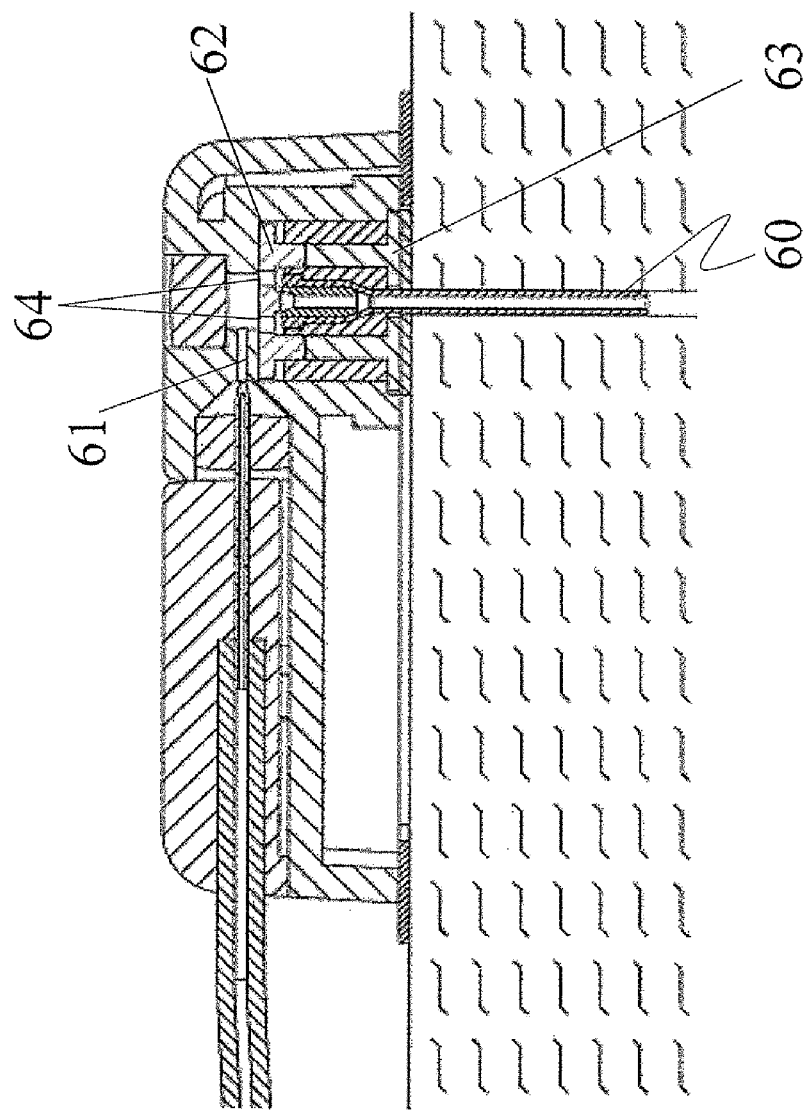
Figure 25:
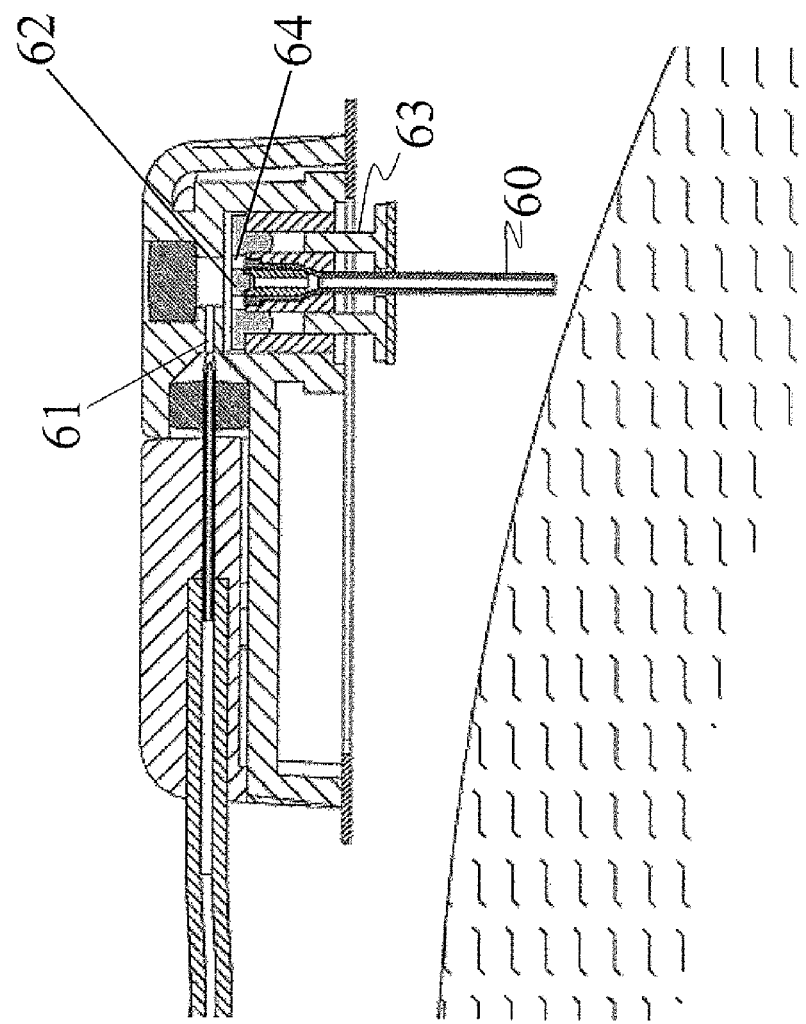

FIGS. 23-25 illustrate a second variant form of a blockage-based embodiment employing a stopper. This variant form includes a cannula 60, a cannula inlet 64, a flow passage 61, a stopper 62 for plugging the cannula inlet 64, a displaceable stopper mount 63 providing vertical 62 mobility. The stopper 62 is made of a sealant material and shaped to plug the cannula inlet thereby preventing the passage of liquids through the cannula. The stopper 62 is mounted on the stopper mount 63 that extends vertically downwards so that when the bottom extremity rests on the patient's body when the infusion set is attached to the body, the mount supporting the stopper 63 maintains the stopper 62 above the cannula inlet 64 thereby enabling the uninhibited flow of liquids through the cannula. As soon as the stopper mount 63 looses contact with the body it moves vertically downwards consequently lowering the attached stopper onto the cannula inlet 64 thereby blockings the passageway to fluid flow. The mount 63 is biased to move downwards via a spring (not shown) so that the default position will be the occluding position.

Figure 26:
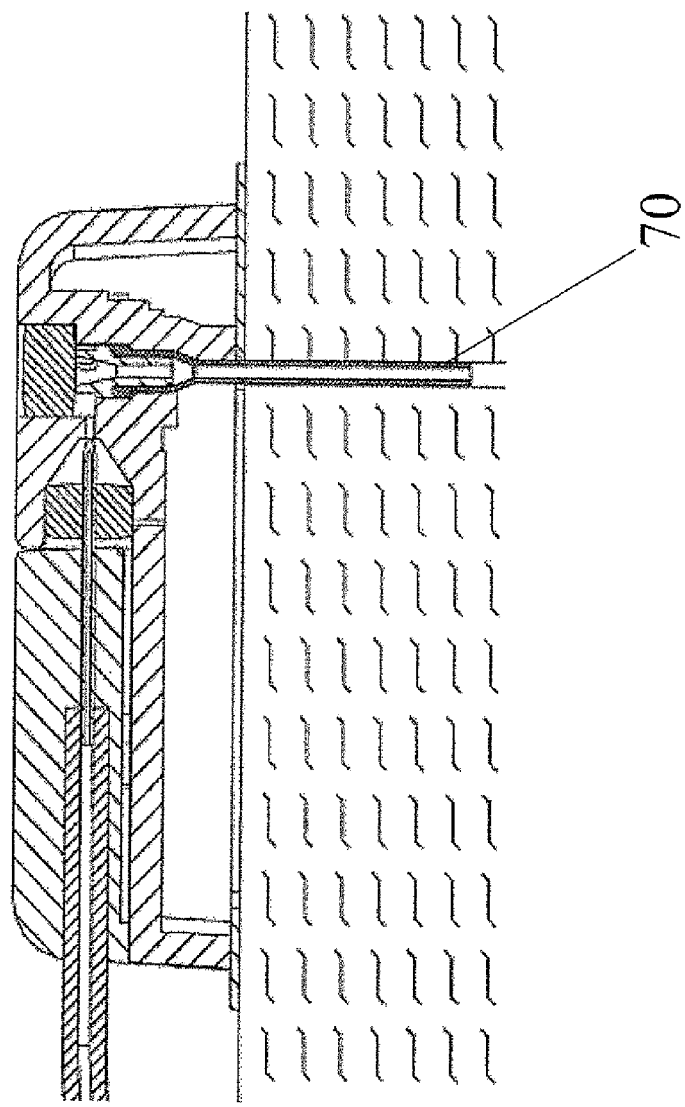
FIGS. 26 and 27 are sectional views of a kink-based embodiment in its non-occluded operational state and detached occluded state, respectively.
Figure 27:
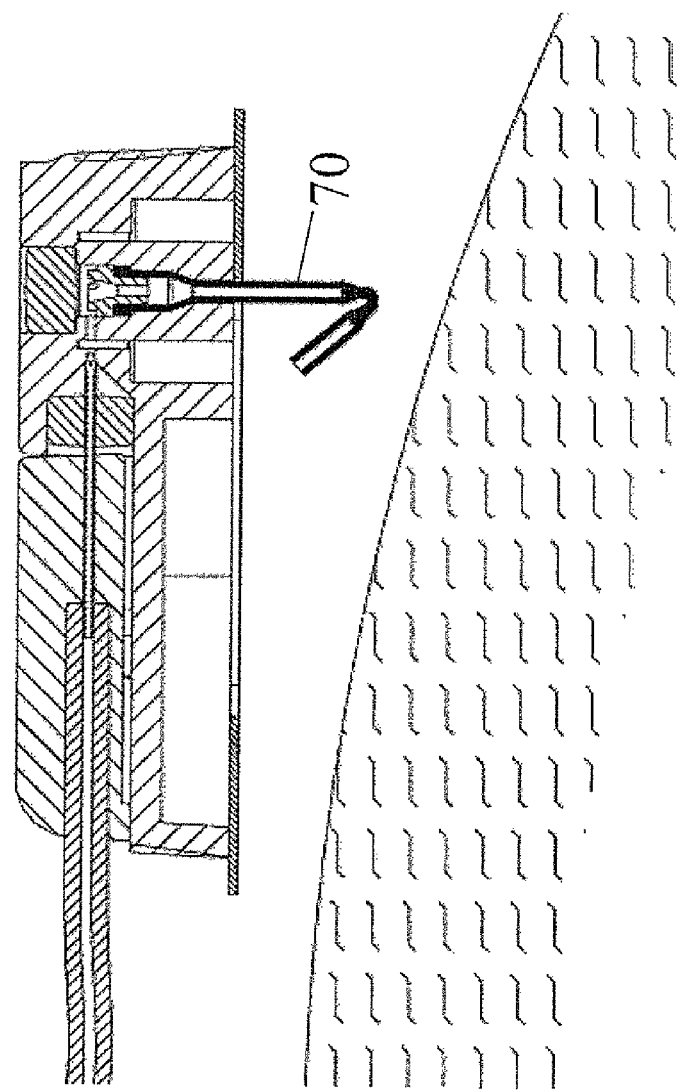

FIGS. 26-27 illustrate a self-kinking embodiment employing a self-kinking cannula 70 in its operative non-occluded state and occluded state respectively. The cannula 70 is inserted in its non-kinked configuration and upon detachment from the patient's body assumes a kinked configuration forming a substantially ninety-degree angle between the two cannula portions connecting at the kink point sufficient to prevent the passage of liquids. This functionality is achieved by forming the cannula 70 from shape memory polymers so as to establish permanent kinked occluding configuration and a temporary operative substantially straight configuration. After insertion in the patient's body, the natural body heat awakens the dormant kinked configuration and is restrained from assuming such a configuration by the patient's body. As soon as the cannula 70 is removed from the body it is free to assume it's kinked, occluding configuration. Alternatively, this functionality may be achieved by forming the cannula 70 into a kinked configuration with sufficient flexibility to be flexed into a straightened operative configuration by an insertion needle.

Figure 28:
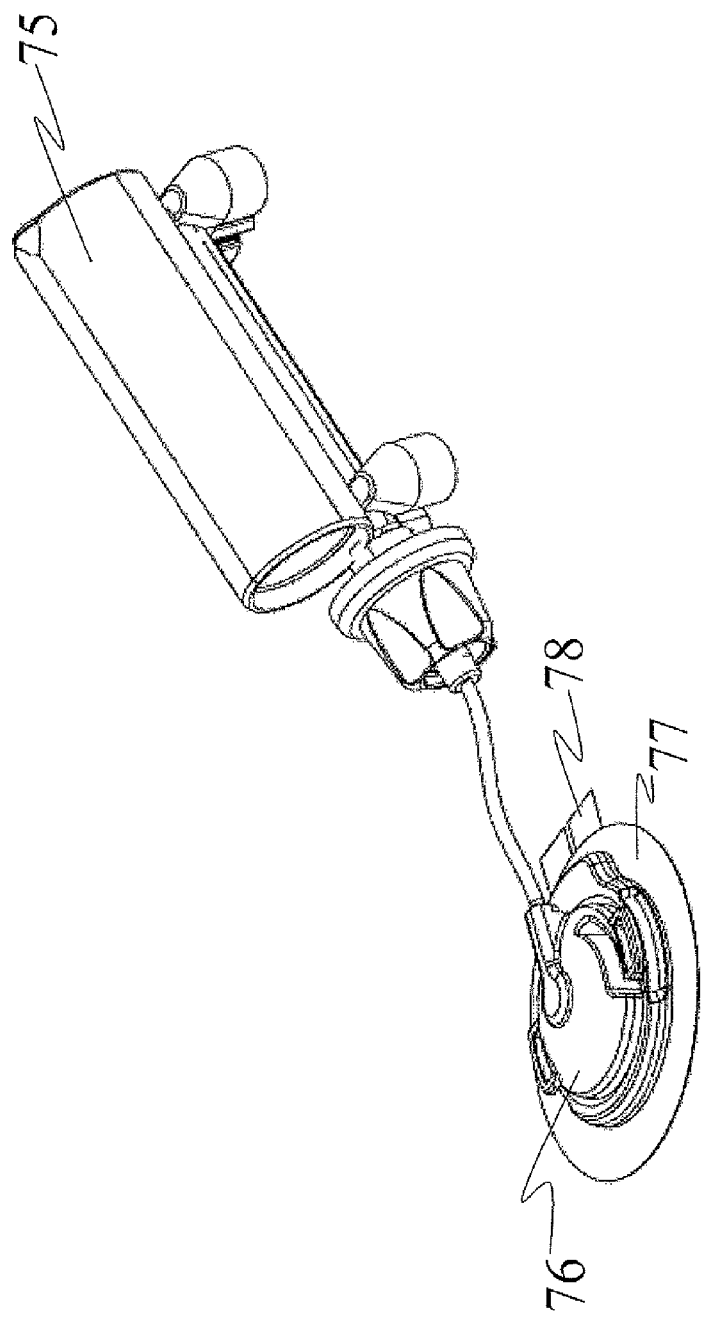
FIG. 28 is an isometric view of an automated medicine delivery system.

A variant form of this kink embodiment employs a constriction mechanism in which the constriction occurs between a flat surface and a sharp edge as most clearly seen in FIGS. 11A and 11B. Such constriction geometry causes the cannula to bend acutely thereby occluding the passage of liquids FIG. 28 depicts the medicine delivery system in which the current invention operates. As illustrated, the system includes a medicine pump 75 connected to an attachable infusion set 76 attached to the patient's body via an adhesive patch 77. Pull-tabs 78 are provided to facilitate removal.

It will be appreciated that the above descriptions are intended only to serve as examples, and that many other possible embodiments are within the scope of the present invention as defined in the appended claims.

What is claimed is:

1. A device for supporting a cannula during administering of a fluid through the skin, the device comprising:
    (a) a base comprising a holder for retaining a cannula in a cannula position suitable for administering a fluid through the skin, said base having a skin contact surface for adhesive attachment to the skin;
    (b) a mechanical sensing element retained in a first position relative to said base by contact with the skin while said skin contact surface is attached to the skin, said mechanical sensing element being displaceable to a second position when said skin contact surface is detached from the skin; and
    (c) an occluding element mechanically biased to move relative to said base from a non-occluding position to an occluding position, said occluding position being such that, when a cannula is retained in said cannula position, said occluding element acts on the cannula to at least partially occlude flow through the cannula, said occluding element being mechanically linked to said mechanical sensing element so as to be selectively retained in said non-occluding position while said mechanical sensing element is in said first position.

2. The device of claim 1, wherein said mechanical sensing element is pivotally linked to said base.

3. The device of claim 1, wherein said occluding element is slidingly engaged with said base so as to slide from said non-occluding position to said occluding position.

4. The device of claim 3, further comprising a compression spring deployed to bias said occluding element to slide from said non-occluding position to said occluding position.

5. The device of claim 3, wherein a direction of said sliding engagement is substantially parallel to said skin contact surface.

6. The device of claim 1, wherein said mechanical sensing element extends on two opposing sides of said cannula position.

7. The device of claim 1, further comprising adhesive deployed on at least said skin contact surface.

8. A device for supporting a cannula during administering of a fluid through the skin, the device comprising:
  (a) a base comprising a holder for retaining the cannula in a cannula position suitable for administering a fluid through the skin, said base having a skin contact surface provided with a layer of adhesive for attachment to the skin;
  (b) a mechanical sensing element pivotally mounted to said base and retained in a first position relative to said base by contact with the skin while said skin contact surface is attached to the skin, said mechanical sensing element being pivotally displaceable to a second position when said skin contact surface is detached from the skin; and
  (c) an occluding element slidingly engaged with said base and mechanically biased to slide from a non-occluding position to an occluding position, said occluding position being such that, when a cannula is retained in said cannula position, said occluding element acts on the cannula retained in said cannula position to at least partially occlude flow through the cannula, said occluding element being mechanically linked to said mechanical sensing element so as to be selectively retained in said non-occluding position while said mechanical sensing element is in said first position.

9. The device of claim 8, further comprising a compression spring deployed to bias said occluding element to slide from said non-occluding position to said occluding position.

10. The device of claim 9, wherein a direction of said sliding engagement is substantially parallel to said skin contact surface.

11. The device of claim 8, wherein said mechanical sensing element extends on two opposing sides of said cannula position.

\* \* \* \* \*